United States Patent
Chivukula et al.

(10) Patent No.: US 10,131,636 B2
(45) Date of Patent: Nov. 20, 2018

(54) PROCESS FOR THE PREPARATION OF ENZALUTAMIDE

(71) Applicant: Laurus Labs Ltd., Hyderabad (IN)

(72) Inventors: Kameswar R. Chivukula, Hyderabad (IN); Veera Venkateswara Rao Karuturi, Hyderabad (IN); Srinivas Benda, Hyderabad (IN); Ramachandra Anke, Hyderabad (IN); Dharmapuri Gajula, Hyderabad (IN); Venkata Rama Krishna Murthy Moturu, Hyderabad (IN); Venkata S. Indukuri, Hyderabad (IN); Seeta Ram Anjaneyulu Gorantla, Hyderabad (IN); Satyanarayana Chava, Hyderabad (IN)

(73) Assignee: Laurus Labs Limited, Hyderadad (IN)

(*) Notice: Subject to any disclaimer, the term of this patent is extended or adjusted under 35 U.S.C. 154(b) by 0 days.

(21) Appl. No.: 15/516,206

(22) PCT Filed: Oct. 1, 2015

(86) PCT No.: PCT/IN2015/000375
§ 371 (c)(1),
(2) Date: Mar. 31, 2017

(87) PCT Pub. No.: WO2016/051423
PCT Pub. Date: Apr. 7, 2016

(65) Prior Publication Data
US 2017/0313662 A1    Nov. 2, 2017

(30) Foreign Application Priority Data

Oct. 1, 2014   (IN) ............... 4958/CHE/2014
Dec. 15, 2014  (IN) ............... 6304/CHE/2014

(51) Int. Cl.
| | | |
|---|---|---|
| *C07D 233/86* | (2006.01) | |
| *C07C 331/28* | (2006.01) | |
| *C07C 333/08* | (2006.01) | |
| *C07C 335/22* | (2006.01) | |
| *C07C 335/26* | (2006.01) | |
| *C07C 22/08* | (2006.01) | |
| *C07C 25/13* | (2006.01) | |
| *C07C 255/49* | (2006.01) | |

(52) U.S. Cl.
CPC ............ *C07D 233/86* (2013.01); *C07C 22/08* (2013.01); *C07C 25/13* (2013.01); *C07C 255/49* (2013.01); *C07C 331/28* (2013.01); *C07C 333/08* (2013.01); *C07C 335/22* (2013.01); *C07C 335/26* (2013.01); *C07C 2601/16* (2017.05)

(58) Field of Classification Search
CPC .................................................... C07D 233/86
See application file for complete search history.

(56) References Cited

U.S. PATENT DOCUMENTS

| | | | | |
|---|---|---|---|---|
| 7,709,517 B2 * | 5/2010 | Sawyers | ............... | C07D 233/70 514/385 |
| 8,110,594 B2 * | 2/2012 | Jung | .................... | C07D 233/86 514/391 |
| 2007/0254933 A1 * | 11/2007 | Jung | .................... | C07D 233/86 514/387 |

FOREIGN PATENT DOCUMENTS

WO    WO2016038560    *   3/2016

OTHER PUBLICATIONS

King et al, abstract of Drug laws and the 'derivative' problem, 2014, Drug Test Anal, vol. 7-8, p. 879-883. (Year: 2014).*

* cited by examiner

*Primary Examiner* — Rebecca L Anderson
*Assistant Examiner* — Karen Cheng
(74) *Attorney, Agent, or Firm* — Blank Rome LLP

(57) ABSTRACT

The present invention relates to an improved process for the preparation of enzalutamide by conventional synthesis, which avoids utilization of microwave irradiation and noxious reagents. The present invention also relates to an improved process for preparation of 4-isothiocyanato-2-(trifluoromethyl) benzonitrile, which is an intermediate in the synthesis of Enzalutamide.

18 Claims, 2 Drawing Sheets

PROCESS FOR THE PREPARATION OF ENZALUTAMIDE

CROSS-REFERENCE TO RELATED APPLICATIONS

This application is a national phase application that is based on and claims the benefit of International Application PCT/IB2015/000375, filed on Oct. 1, 2015, which is based on and claims the benefit of Indian Provisional Application No. 4958/CHE/2014, filed Oct. 1, 2014, entitled "An improved process for the preparation of enzalutamide" and Indian Provisional Application No. 6304/CHE/2014 filed Dec. 15, 2015 entitled "An improved process for preparation of 4-isothiocyanato-2-(trifluromethyl) benzonitrile", the contents of each of which is incorporated by reference herein.

FIELD OF THE INVENTION

The present invention generally relates to an improved process for the preparation of Enzalutamide. Particularly, the present invention relates to conventional synthesis of enzalutamide, which avoids utilization of microwave irradiation.

The present invention also relates to a process for preparation of 4-isothiocyanato-2-(trifluoromethyl) benzonitrile, an intermediate for preparation of Enzalutamide.

BACKGROUND OF THE INVENTION

Enzalutamide, also known as 4-{3-[4-cyano-3-(trifluoromethyl) phenyl]-5,5-dimethyl-4-oxo-2-sulfanylideneimidazolidin-1-yl}-2-fluoro-N-methylbenzamide, is represented by the following structure of Formula I:

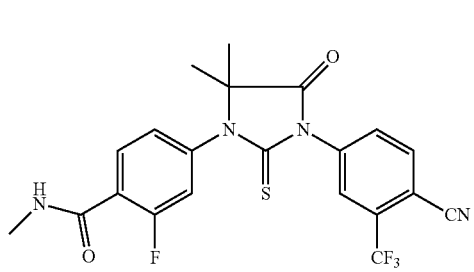

Formula I

Enzalutamide is marketed by Astellas under the trade name XTANDI® is a androgen receptor inhibitor for the treatment of patients with metastatic castration-resistant prostate cancer who have previously received docetaxel.

U.S. Pat. No. 7,709,517 ("the '517 patent") discloses a variety of diarylhydantoin compounds and their derivatives such as enzalutamide. The '517 patent discloses a process for preparation of enzalutamide by preparation of 4-isothiocyanato-2-trifluoro methyl benzonitrile of Formula 3 from 4-amino-2-trifluoromethyl benzonitrile of Formula 2 using thiophosgene followed by cyclization of the Formula 3 with N-methyl-2-fluoro-4-(1,1-dimethyl-cyanomethyl)-amino benzamide of Formula 4 by microwave irradiation at a temperature of about 100° C. for about 11 hr to obtain enzalutamide, which is purified by silica gel column chromatography with a mixture of methylene chloride:acetone. The process disclosed in the '517 patent is schematically represented as follows:

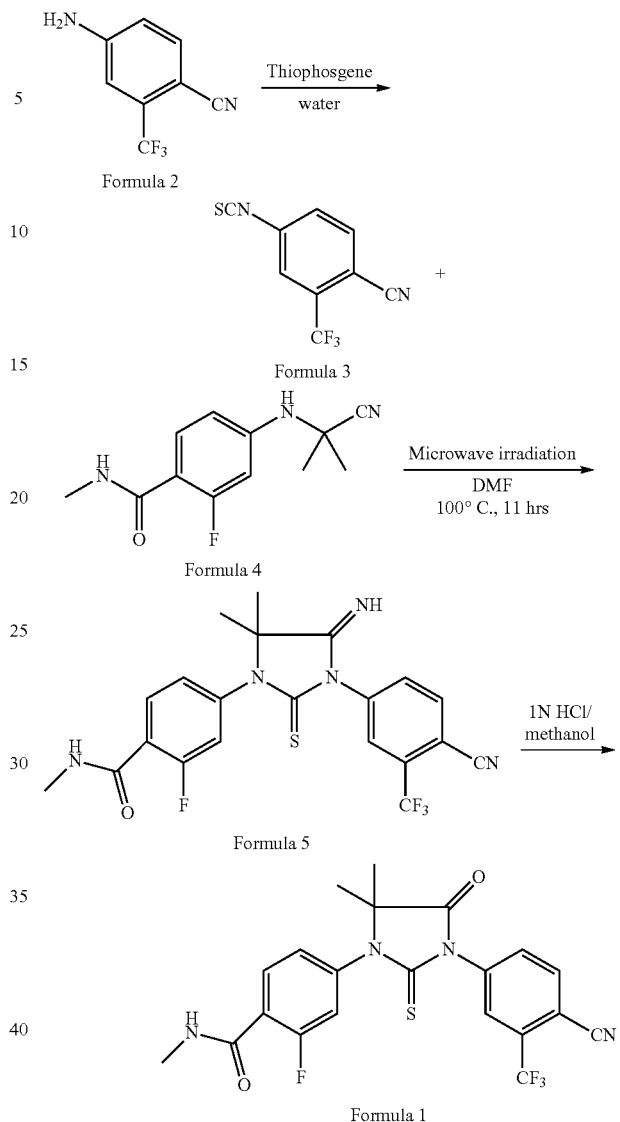

The synthesis of enzalutamide as disclosed in the '517 patent has certain drawbacks as it involves:

a) preparation of isothiocyanate intermediate of Formula 3 involves highly noxious reagent such as thiophosgene, which is an insidious poison and it generates high amount of poisonous phosgene gas and is difficult to control, particularly on commercial scale and thus requires more labor and utmost care to use;

b) cyclization of compound of formula 3 and formula 4 involves microwave irradiation at 100° C. for a period of about 11 hr gave less yields of about only 25%. The use of special techniques such as reaction by microwave irradiation is not viable for commercial scale operations as this technique involves specialized expensive equipments;

c) further formation of high amounts of un-cyclized impurity of Formula 1A and urea by-product of Formula 3B as an impurities in the cyclization reaction and thus additional purification steps are required to remove; and

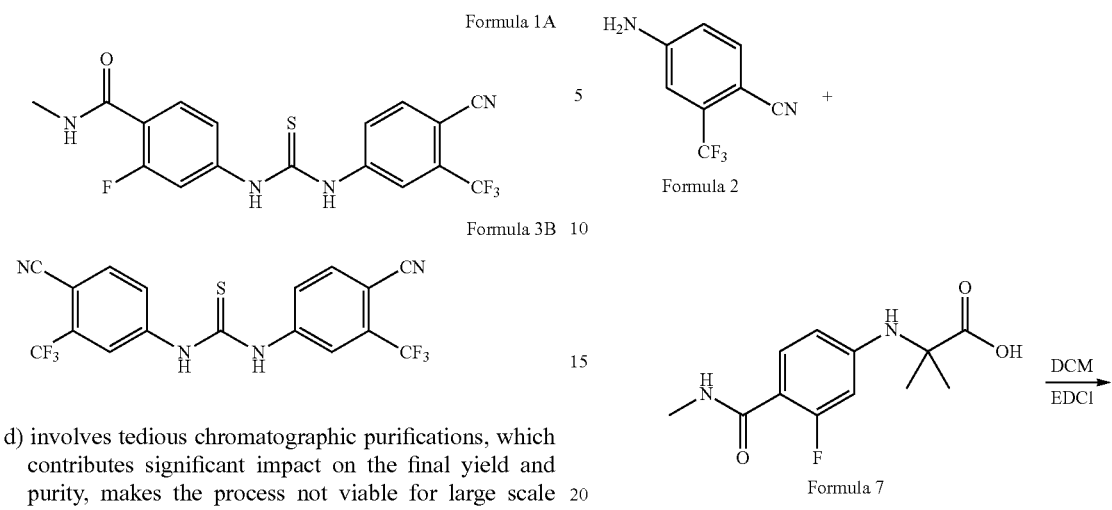

d) involves tedious chromatographic purifications, which contributes significant impact on the final yield and purity, makes the process not viable for large scale manufacturing.

Patent publication No. WO2011/106570 ("the '570 publication") disclosed an alternate process for preparation of enzalutamide by cyclization of 4-isothiocyanato-2-trifluoro methyl benzonitrile of Formula 3 and methyl-2-(3-fluoro-4-(methylcarbamoyl) phenylamino)-2-methylpropanoate of Formula 6 in a mixture of dimethylsulfoxide:isopropyl acetate for a period of about 17.5 hours. The process disclosed in the '570 publication is schematically represented as follows:

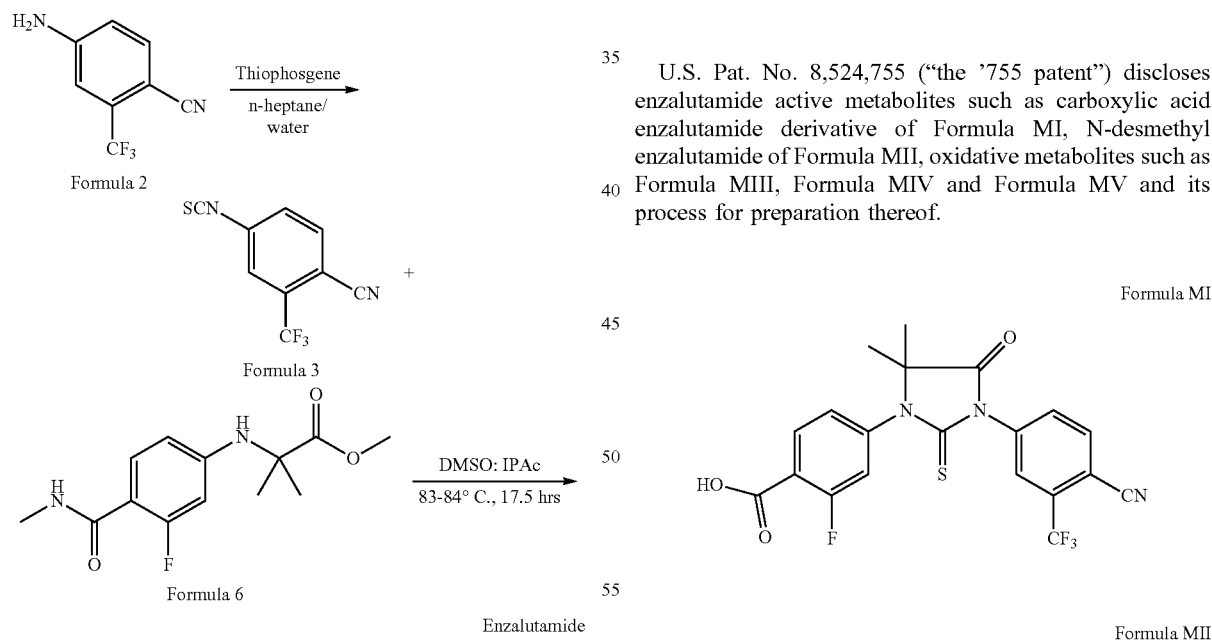

The '570 publication also discloses preparation of enzalutamide by coupling of 4-amino-2-(trifluoromethyl) benzonitrile of Formula 2 and 2-{[3-fluoro-4-(methyl carbamoyl) phenyl]amino}-2-methylpropanoic acid of Formula 7 in presence of a coupling reagent EDCl and followed by cyclization in presence of highly noxious thiophosgene. The process disclosed in the '570 publication is schematically represented as follows:

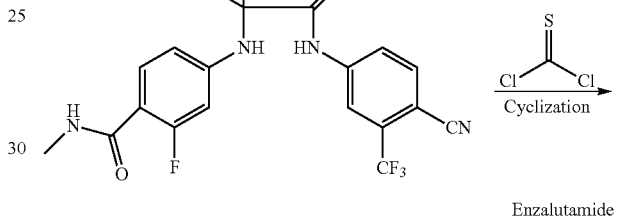

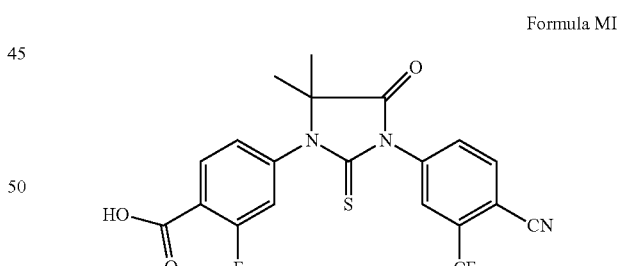

U.S. Pat. No. 8,524,755 ("the '755 patent") discloses enzalutamide active metabolites such as carboxylic acid enzalutamide derivative of Formula MI, N-desmethyl enzalutamide of Formula MII, oxidative metabolites such as Formula MIII, Formula MIV and Formula MV and its process for preparation thereof.

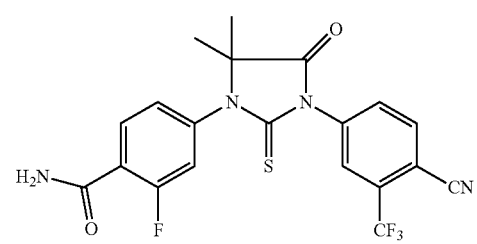

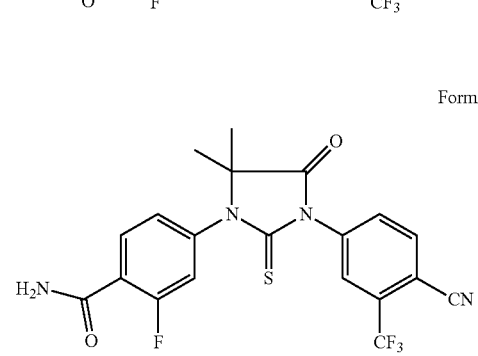

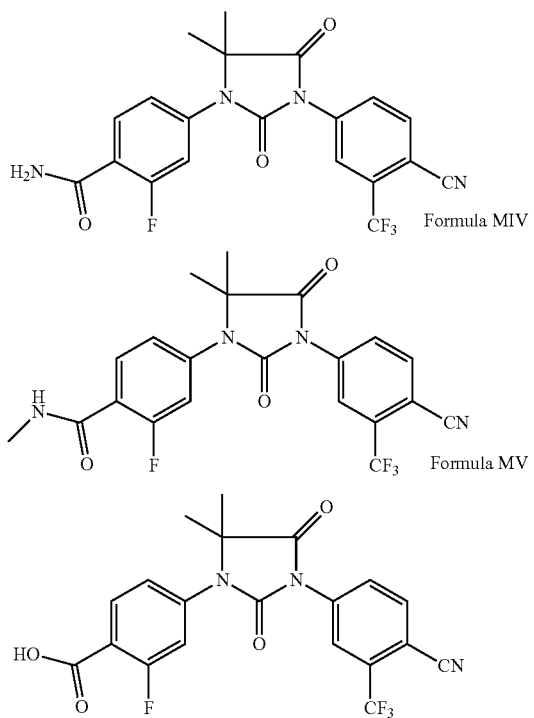

Patent publication No.(s) WO2015/063720, WO2015/121768, CN103910679, CN103980141, CN104016924 and CN104710367 disclosed process for preparation of enzalutamide by final cyclization of 4-isothiocyanato-2-trifluoro methyl benzonitrile of Formula 3 and methyl-2-(3-fluoro-4-(methylcarbamoyl) phenylamino)-2-methyl propanoate of Formula 6 by the same process disclosed in '570 publication.

Patent publication No. WO2015/092617 ("the '617 publication") disclosed process for preparation of enzalutamide by cyclization of benzotriazole or succinamide ester intermediate with o-phenyl[4-cyano-3-(trifluoromethyl)phenyl] carbamothioate or 4-isothiocyanato-2-trifluoro methyl benzonitrile in a mixture of dimethylsulfoxide:isopropyl acetate. The process disclosed in the '617 publication is schematically represented as follows:

U.S. publication No. US2015/0210649 ("the '649 publication") disclosed process for preparation of enzalutamide by cyclization of acid intermediate of Formula 7 with 4-isothiocyanato-2-trifluoro methyl benzonitrile in presence of phenol in chloroform. The process disclosed in the '649 publication is schematically represented as follows:

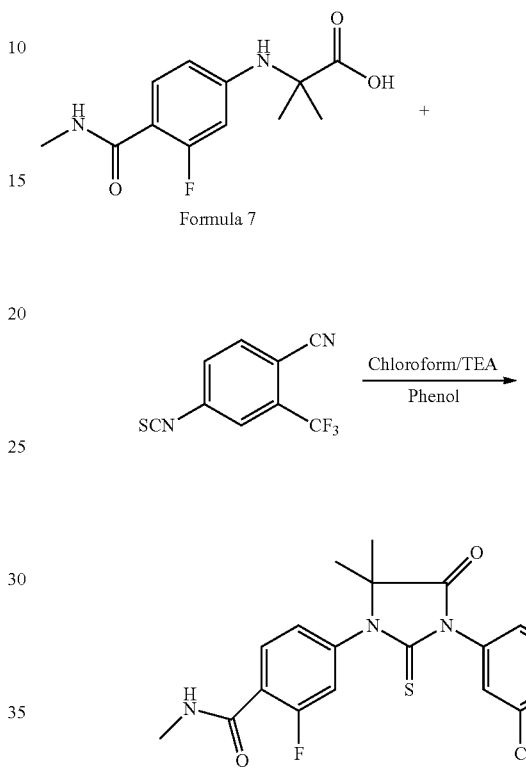

C.N. publication No. (s) 104803918 ("the '918 publication") and 104803919 ("the '919 publication") disclosed process for preparation of enzalutamide by cyclization of diester intermediate with 4-isothiocyanato-2-trifluoro methyl benzonitrile and finally conversion of ester in to N-methyl amide in presence of methylamine. The process disclosed in the above publications is schematically represented as follows:

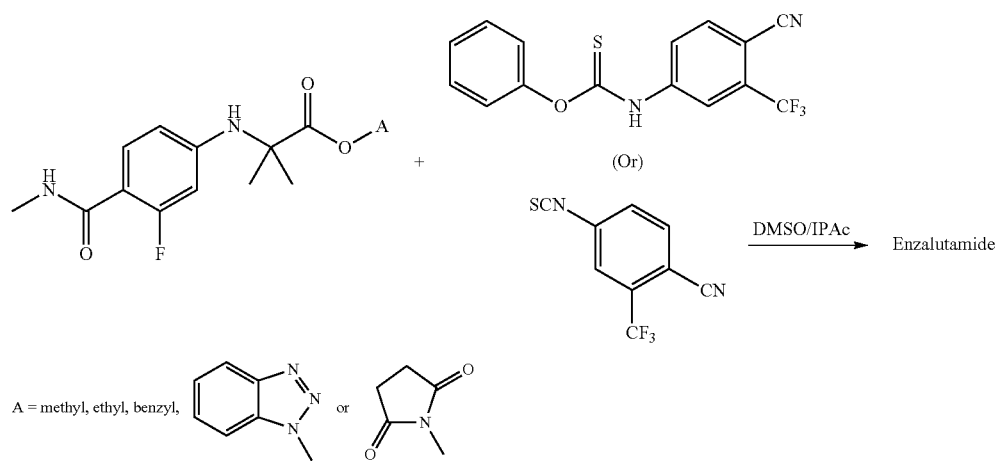

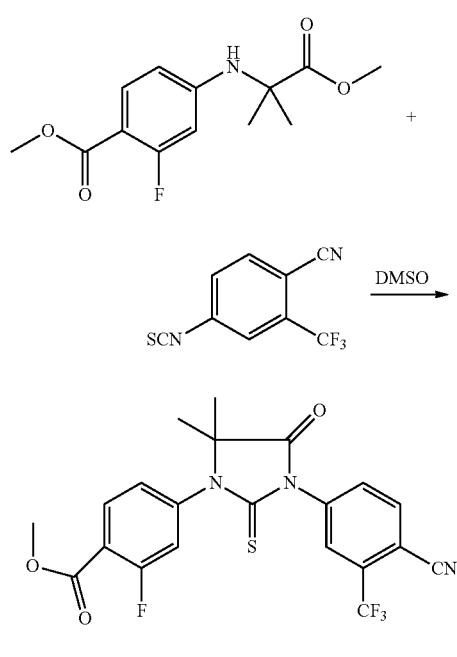

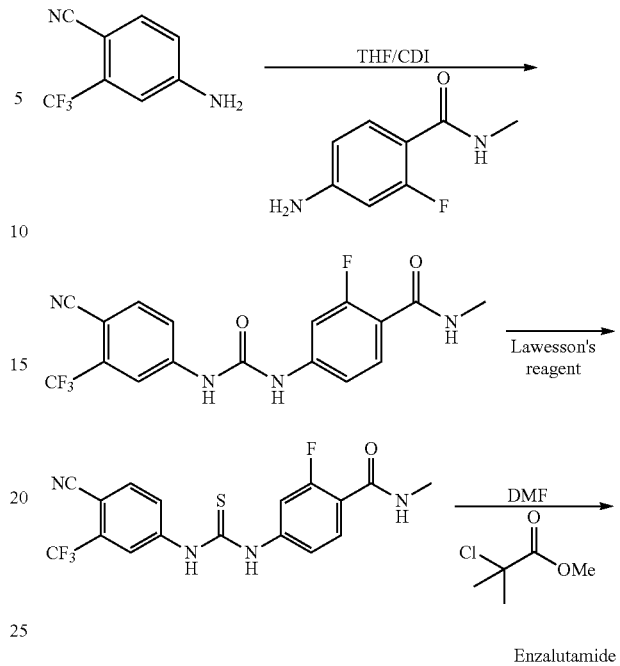

C.N. publication No. 104844520 ("the '520 publication") disclosed process for preparation of enzalutamide by reaction of hydantoin intermediate with bromo intermediate at final stage. The process disclosed in the '520 publications is schematically represented as follows:

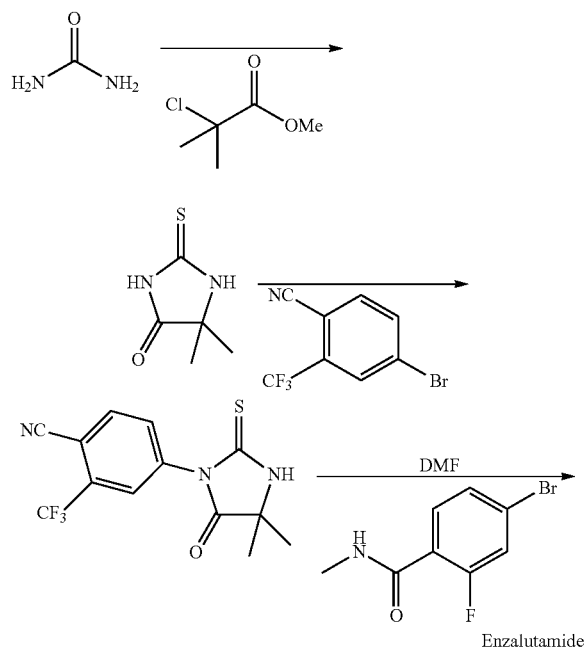

C.N. publication No. 104844521 ("the '521 publication") disclosed process for preparation of enzalutamide by cyclization of hydantoin ring at final stage. The process disclosed in the '521 publications is schematically represented as follows:

Based on the drawbacks mentioned above, there is a vital need to develop a process for the preparation of enzalutamide and its intermediates, which is readily amenable to large scale production.

Hence, present inventors focused research to simplify the process for the preparation of enzalutamide, which avoids mainly microwave irradiation and making the process more suitable for commercial applications with higher purity and obviate the problems associated with the reported process as well as avoiding noxious and expensive reagent such as thiophosgene.

SUMMARY OF THE INVENTION

In accordance with one embodiment, the present invention provides an improved process for the preparation of enzalutamide of Formula I,

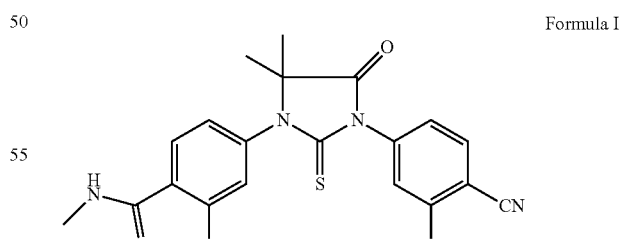

Formula I comprising:
a) reacting 4-Amino-2-trifluoromethyl benzonitrile of Formula 2 with a source of isothiocyanate of Formula P—NCS, to obtain a compound of Formula 8; wherein 'P' represents hydrogen or a protective derivative thereof,

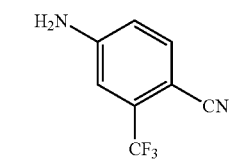

Formula 2

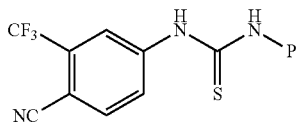

Formula 8 b) optionally deprotecting the compound of Formula 8 to obtain a compound of Formula 9,

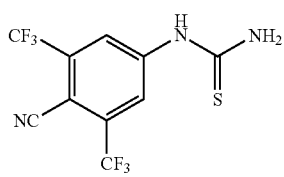

Formula 9 c) heating the compound of Formula 9 to obtain a compound of Formula 3,

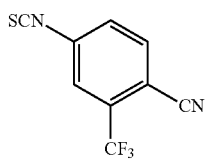

Formula 3 d) reacting the compound of Formula 3 with a compound of Formula 4 in a suitable solvent system to obtain a compound of Formula 5, and

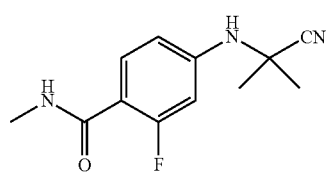

Formula 4

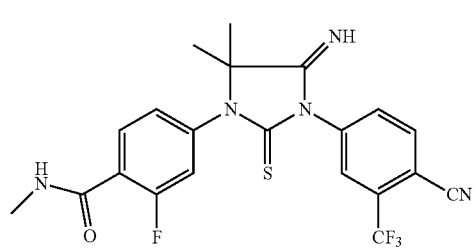

Formula 5 e) reacting the compound of Formula 5 with an acid in a suitable organic solvent to obtain enzalutamide.

In accordance with another embodiment, the present invention provides an improved process for the preparation of enzalutamide of Formula I, comprising:

a) reacting 4-Amino-2-trifluoromethyl benzonitrile of Formula 2 with a source of isothiocyanate of Formula P—NCS, to obtain a compound of Formula 8; wherein 'P' represents hydrogen or a protective derivative thereof, b) optionally deprotecting the compound of Formula 8 to obtain a compound of Formula 9, c) heating the compound of Formula 9 to obtain a compound of Formula 3, and d) converting the compound of Formula 3 into enzalutamide.

In accordance with another embodiment, the present invention provides an improved process for the preparation of enzalutamide of Formula I, comprising:

a) reacting 4-Amino-2-trifluoromethyl benzonitrile of Formula 2 with benzoyl isothiocyanate to obtain a compound of Formula 8a,

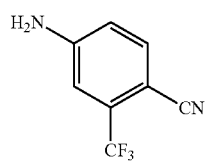

Formula 2

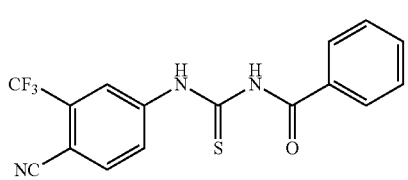

Formula 8a b) deprotecting the compound of Formula 8a to obtain a compound of Formula 9, and

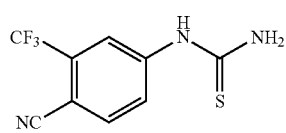

Formula 9 c) heating the compound of Formula 9 to obtain a compound of Formula 3, and

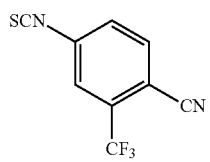

Formula 3 d) converting the compound of Formula 3 into enzalutamide.

In accordance with another embodiment, the present invention provides an improved process for the preparation of enzalutamide of Formula I, comprising:

i) reacting 4-Amino-2-trifluoromethyl benzonitrile of Formula 2 with thiocarbonyldiimidazole (TCDI) in a suitable solvent in presence of a suitable base to obtain a compound of Formula 3, Formula 2

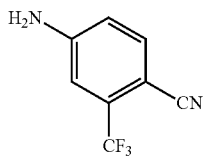

TCDI

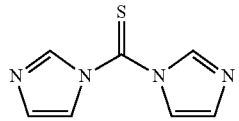

Formula 3

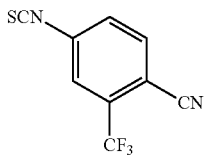

ii) reacting the compound of Formula 3 with a compound of Formula 4 in a suitable solvent system to obtain a compound of Formula 5, and Formula 4

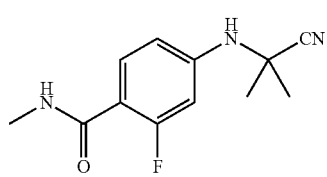

Formula 5

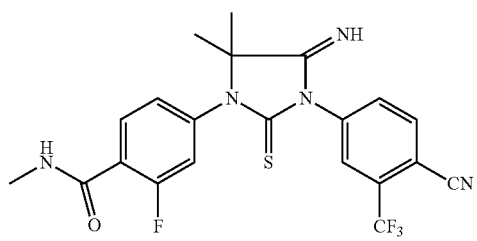

iii) reacting the compound of Formula 5 with an acid in a suitable organic solvent to obtain enzalutamide.

In accordance with another embodiment, the present invention provides an improved process for the preparation of enzalutamide of Formula I, comprising:
  a1) reacting 4-Amino-2-trifluoromethyl benzonitrile of Formula 2 with thiocarbonyldiimidazole (TCDI) in a suitable solvent in presence of a suitable base to obtain a compound of Formula 3, and
  b1) converting the compound of Formula 3 into enzalutamide.

In accordance with another embodiment, the present invention provides an improved process for the preparation of enzalutamide of Formula I, comprising:
  a2) reacting 4-isothiocyanato-2-trifluoro methyl benzonitrile of Formula 3 with N-methyl-2-fluoro-4-(1,1-dimethyl-cyanomethyl)-amino benzamide of Formula 4 in a suitable solvent system to obtain, a compound of Formula 5, and
  b2) reacting the compound of Formula 5 with an acid in a suitable organic solvent to obtain enzalutamide.

In accordance with another embodiment, the present invention provides an improved process for the preparation of enzalutamide of Formula I, comprising:
  a2) reacting a compound of Formula 3 with a compound of Formula 4 in a suitable solvent system to obtain a compound of Formula 5, and
  b2) reacting the compound of Formula 5 with an acid in a suitable organic solvent to obtain enzalutamide; wherein the suitable solvent system is selected from the group comprising polar solvents such as amides, nitriles, ethers, esters, sulfones, water and the like and mixtures thereof.

In accordance with another embodiment, the present invention provides a process for purification of enzalutamide of Formula I, comprising:
  a3) dissolving enzalutamide in one or more organic solvents at a suitable temperature, and
  b3) isolating the pure enzalutamide.

In accordance with another embodiment, the present invention provides a process for purification of 4-isothiocyanato-2-(trifluoromethyl) benzonitrile of Formula 3, comprising:
  i) dissolving 4-isothiocyanato-2-(trifluoromethyl) benzonitrile of Formula 3 in a suitable solvent at a suitable temperature,
  ii) filtering the step i) solution,
  iii) optionally concentrating the filtrate,
  iv) cooling to less than 10° C., and
  v) isolating the pure compound of Formula 3.

In accordance with another embodiment, the present invention provides compound of Formula 3 substantially free of one or more of following compounds:

Formula 3A

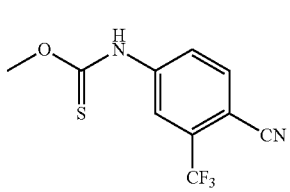

Formula 3B

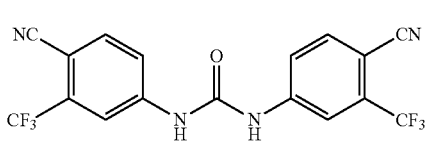

Formula 3C

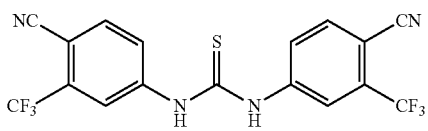

In accordance with another embodiment, the present invention provides enzalutamide of Formula I substantially free of one or more of following compounds:

Formula 3A
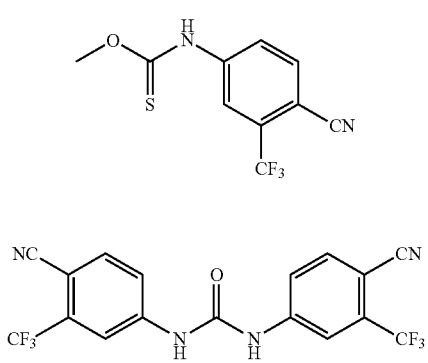

Formula 3B
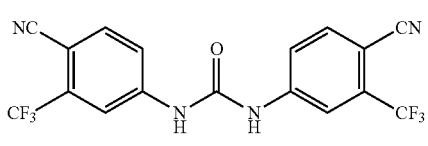

Formula 3C
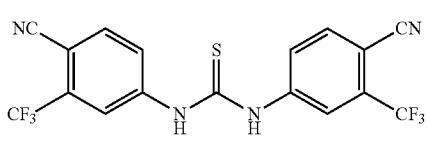

Formula 1A
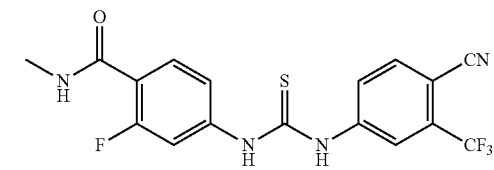

Formula MI
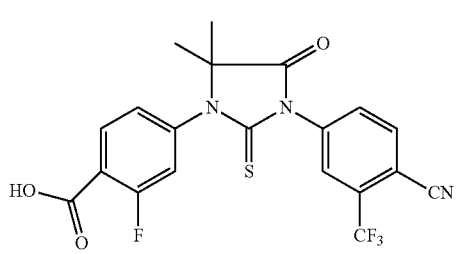

Formula MIV
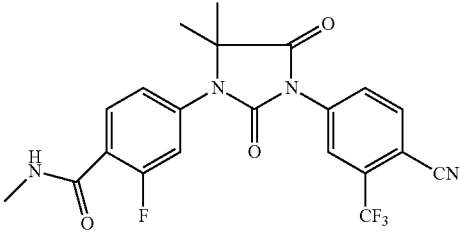

Formula MV
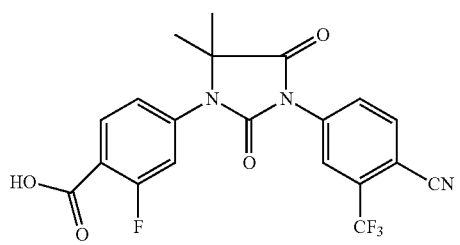

In accordance with another embodiment, the present invention provides a compound of Formula 1A Formula 1A
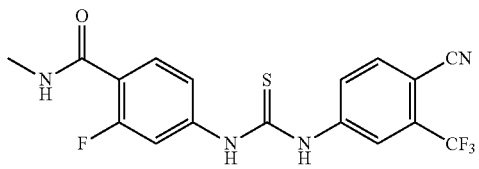

In accordance with another embodiment, the present invention provides a compound of Formula 3A Formula 3A
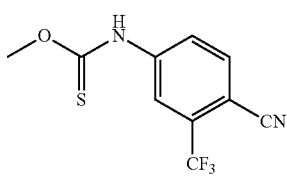

In accordance with another embodiment, the present invention provides a compound of Formula 3B Formula 3B
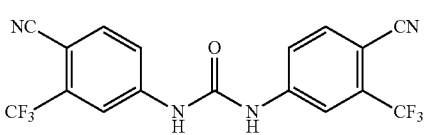

In accordance with another embodiment, the present invention provides a compound of Formula 3C Formula MII
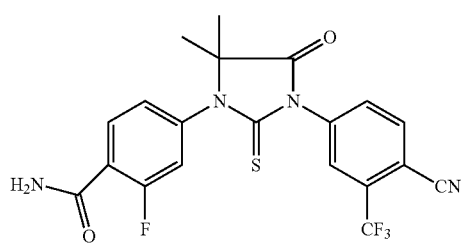

Formula MIII
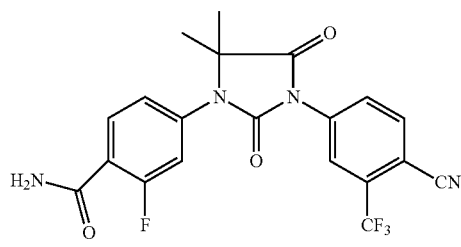

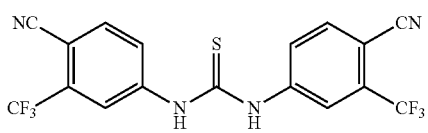
Formula 3C

In accordance with another embodiment, the present invention provides a compound of Formula 8

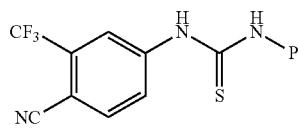
Formula 8 wherein 'P' represents hydrogen or a protective derivative thereof.

In accordance with another embodiment, the present invention provides a compound of Formula 8

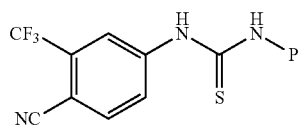
Formula 8 wherein 'P' represents hydrogen, R—CO—, R—CO—O—, R—SO$_2$—; wherein R is selected from the group comprising alkyl, alkoxy, haloalkyl, aryl, aralkyl, aryloxy.

In accordance with another embodiment, the present invention provides a compound of Formula 8a

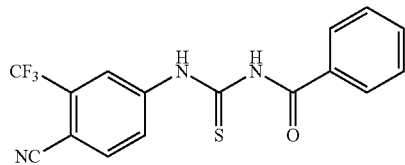
Formula 8a

In accordance with another embodiment, the present invention provides a compound of Formula 9

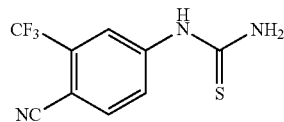
Formula 9

In accordance with another embodiment, the present invention provides a pharmaceutical composition, comprising enzalutamide prepared by the processes of the present invention and at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
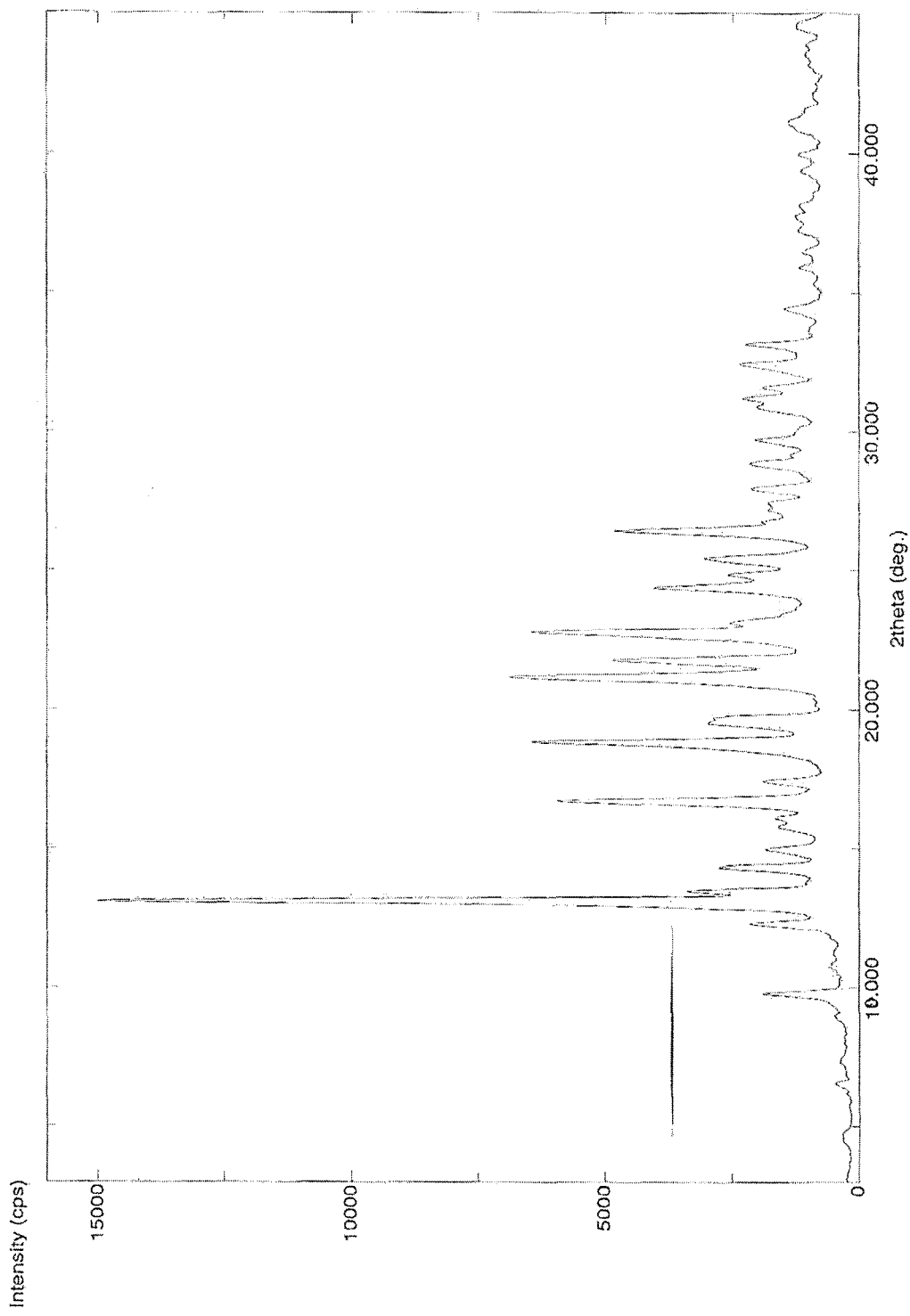
FIG. 1 is the characteristic powder X-ray diffraction (XRD) pattern of enzalutamide, prepared according to Example 6.

The present invention encompasses an improved process for the preparation of enzalutamide and intermediates thereof with high product yield and quality, wherein the improvements comprise use of conventional synthesis, which avoids cumbersome microwave irradiation during the cyclization of 4-isothiocyanato-2-(trifluoro methyl) benzonitrile of Formula 3 and N-methyl-2-fluoro-4-(1,1-dimethylcyanomethyl)-amino benzamide of Formula 4; and further avoids use of noxious agents such as thiophosgene in the preparation of isothiocyanate of Formula 3, thereby process more convenient and economical, particularly on industrial scale manufacturing.

In accordance with one embodiment, the present invention provides an improved process for the preparation of enzalutamide of Formula I, comprising:

a) reacting 4-Amino-2-trifluoromethyl benzonitrile of Formula 2 with a source of isothiocyanate of Formula P—NCS, to obtain a compound of Formula 8; wherein 'P' represents hydrogen or a protective derivative thereof,

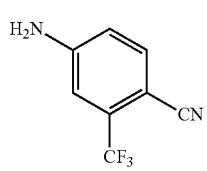
Formula 2

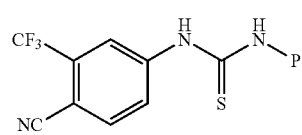
Formula 8 b) optionally deprotecting the compound of Formula 8 to obtain a compound of Formula 9,

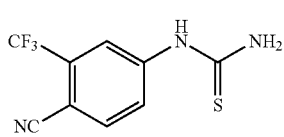
Formula 9 c) heating the compound of Formula 9 to obtain a compound of Formula 3,

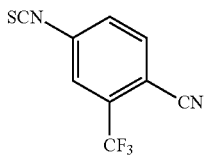

Formula 3 d) reacting the compound of Formula 3 with a compound of Formula 4 in a suitable solvent system to obtain a compound of Formula 5, and

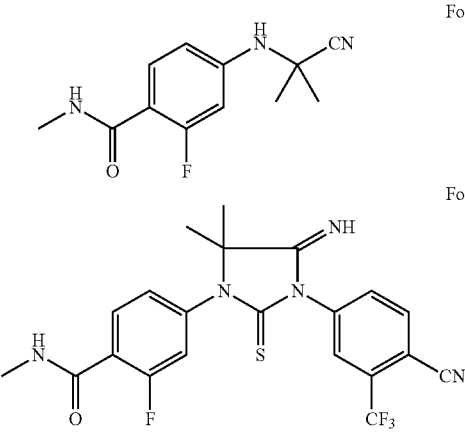

Formula 4

Formula 5 e) reacting the compound of Formula 5 with an acid in a suitable organic solvent to obtain enzalutamide.

The reported literatures disclose a process for preparation of isothiocyanate of Formula 3 by reaction of 4-Amino-2-trifluoromethyl benzonitrile of Formula 2 with highly noxious reagent such as thiophosgene, which is an insidious poison and it generates high amount of poisonous phosgene gas and is difficult to control, particularly on commercial scale and thus requires more labor and utmost care to use.

To overcome the difficulties associated with the processes described above, the inventors of the present invention have developed an alternative process which avoids use of highly noxious reagent such as thiophosgene.

In another embodiment, the starting material of source of isothiocyanate of Formula P—NCS; wherein 'P' represents hydrogen or a protective derivative thereof; can be prepared by a process comprising reacting a suitable salt of thiocyanate with a compound of Formula "P—X"; wherein 'P' represents hydrogen, R—CO—, R—CO—O—, R—SO2-; wherein R is selected from the group comprising alkyl, alkoxy, haloalkyl, aryl, aralkyl, aryloxy and 'X' represents fluoro, chloro, bromo, iodo to obtain a compound of Formula P—NCS; preferably Formula P—NCS is represented as:

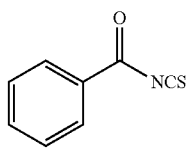

Formula P-NCS

The compound of Formula 4 is known in the art and can be produced by methods known and recognized by the organic chemist of ordinary skill in the art. For example, such a process is described in U.S. Pat. No. 7,709,517 which is included by reference herein in its entirety.

Unless otherwise specified the term "alkyl" used herein the specification represents $C_1$ to $C_5$ alkyl and is selected from the group comprising methyl, ethyl, propyl, isopropyl, butyl, tert-butyl and the like.

Unless otherwise specified the term "alkoxy" used herein the specification represents $C_1$ to $C_5$ alkoxy and is selected from the group comprising methoxy, ethoxy, butoxy, tert-butoxy and the like.

Unless otherwise specified the term "haloalkyl" used herein the specification represents any alkyl radical having one or more hydrogen atoms replaced by a halogen atom and is selected from the group comprising trifluoromethyl, difluoromethyl, trichloromethyl and the like.

Unless otherwise specified the term "aryl" used herein the specification represents aryl refers to any functional group or substituent derived from an aromatic ring and is selected from the group comprising phenyl, naphthyl; optionally substituted with chloro, bromo, fluoro, iodo, methoxy, nitro and the like.

Unless otherwise specified the term "aralkyl" used herein the specification represents an alkyl group substituted with an aryl group (e.g., an aromatic or heteroaromatic group) and is selected from the group comprising benzyl or substituted benzyl, wherein the substituent's are selected from nitro, methoxy, aryl and the like.

Unless otherwise specified the term "suitable salt of thiocyanate" used herein the specification is selected from the group comprising ammonium thiocyanate, lithium thiocyanate, sodium thiocyanate, potassium thiocyanate, cesium thiocyanate, magnesium thiocyanate, calcium thiocyanate, barium thiocyanate, cobalt thiocyanate, lead thiocyanate, mercury thiocyanate and the like; preferably ammonium thiocyanate.

The reaction of a suitable salt of thiocyanate with a compound of Formula "P—X"; wherein 'P' and 'X' are defined as above, may be carried out in a suitable solvent.

In another embodiment, the compound of Formula "P—X" is selected from the group comprising hydrogen chloride, hydrogen bromide, acetyl chloride, acetyl bromide, acetyl iodide, acryloyl chloride, adipoyl chloride, anisoyl chloride, p-methoxy benzoyl chloride, p-methoxy benzoyl bromide, p-nitro benzoyl chloride, p-nitro benzoyl bromide, benzoyl chloride, benzoyl bromide, benzoyl iodide, benzyl chloroformate, tert-butyl chloroformate, methanesulfonyl chloride, ethanesulfonyl chloride, bromodifluoroacetylchloride, butyryl chloride, trichloroacetyl chloride, trifluoroacetyl chloride and the like; preferably hydrogen chloride, acetyl chloride, or benzoyl chloride.

The suitable solvent includes but is not limited to ethers, ketones, halogenated solvents, water and mixtures thereof. Preferably ethers include, but are not limited to tetrahydrofuran, dimethyl ether, diisopropyl ether, methyl tertiary butyl ether, 1,4-dioxane and the like; ketones include, but are not limited to acetone, methyl ethyl ketone, methyl isobutyl ketone and the like; halogenated solvents include, but are not limited to methylene chloride, ethylene chloride and the like; water and mixtures thereof; preferably acetone, methyl tertiary butyl ether or tetrahydrofuran; more preferably acetone.

The reaction of a suitable salt of thiocyanate, preferably ammonium thiocyanate with a compound of Formula "P—X", preferably benzoyl chloride is carried out at a temperature of about 25° C. to reflux temperature; preferably at about 25° C. to 35° C.

After completion of the reaction, the resultant compound of Formula P—NCS can be isolated from the reaction mass as solid by methods known in the art or the product containing existing solution may be used for the subsequent processing steps without isolating the compound; preferably the compound of Formula P—NCS, wherein 'P' defined as above, is converted directly to the next step without further workup.

The step a) of aforementioned process involves reaction of 4-Amino-2-trifluoromethyl benzonitrile of Formula 2 with a source of isothiocyanate of Formula P—NCS, obtained by the process described as above or obtained directly from the commercial sources, to obtain a compound of Formula 8; wherein 'P' defined as above, advantageously carried out in a suitable solvent.

In a preferred embodiment, the compound of Formula 8 specifically represented as following Formula 8a:

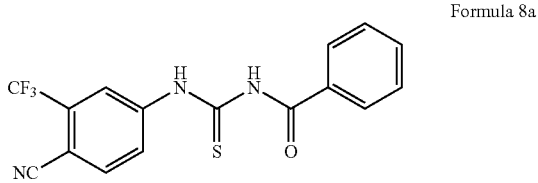 [SMILES: N#Cc1ccc(NC(=S)NC(=O)c2ccccc2)cc1C(F)(F)F]

Formula 8a

The suitable solvent used herein for step a) includes but is not limited to ethers, ketones, halogenated solvents, water and mixtures thereof. Preferably ethers include, but are not limited to tetrahydrofuran, dimethyl ether, diisopropyl ether, methyl tertiary butyl ether, 1,4-dioxane and the like; ketones include, but are not limited to acetone, methyl ethyl ketone, methyl isobutyl ketone and the like; halogenated solvents include, but are not limited to methylene chloride, ethylene chloride and the like; water and mixtures thereof; preferably acetone, methyl tertiary butyl ether or tetrahydrofuran; more preferably acetone.

The reaction of 4-Amino-2-trifluoromethyl benzonitrile of Formula 2 with a source of isothiocyanate of Formula P—NCS; where in "P" defined as above; is carried out at a temperature of about 25° C. to reflux temperature; preferably at about 40° C. to 70° C.

After completion of the reaction, the resultant compound of Formula 8 may be isolated from the reaction mass or may be directly proceed for the next step. Preferably, compound of Formula 8 is isolated as solid, which process includes saturating the reaction mass by adding suitable anti solvent such as water to precipitating out the compound of Formula 8; where in "P" defined as above.

Step b) of aforementioned process involves optional deprotection of the compound of Formula 8; when the "P" represents other than hydrogen, preferably benzoyl group; to obtain a compound of Formula 9.

The deprotection step may be carried out in presence of a suitable base and in a suitable organic solvent.

The suitable base used herein for deprotection include but is not limited to inorganic bases selected from alkali metal hydroxides such as lithium hydroxide, sodium hydroxide, potassium hydroxide and the like; alkali metal alkoxides such as sodium methoxide, sodium ethoxide, sodium tert-butoxide, potassium tert-butoxide and the like; alkali metal carbonates such as sodium carbonate, potassium carbonate, cesium carbonate and the like; alkali metal bicarbonates such as sodium bicarbonate, potassium bicarbonate and the like; and organic bases selected from the group consisting of triethylamine, isopropyl ethylamine, diisopropyl amine, diisopropyl ethylamine, N-methyl morpholine, piperidine, pyridine and the like; guanidine bases such as 1,1,3,3-Tetramethylguanidine (TMG) and the like and mixtures thereof; preferably sodium hydroxide or potassium hydroxide.

The source of base can be added either as solution in water or it may be added as solid to the solution of reaction mixture.

The suitable organic solvent used herein for deprotection includes but is not limited to alcohols, ketones, ethers, halogenated hydrocarbons and mixtures thereof. The alcohols include, but are not limited to methanol, ethanol, propanol, isopropanol and the like; ketones include, but are not limited to acetone, methyl isobutyl ketone, methyl ethyl ketone and the like; ethers include, but are not limited to tetrahydrofuran, dimethyl ether, diisopropyl ether, methyl tertiary butyl ether, 1,4-dioxane and the like; halogenated hydrocarbons include, but are not limited to methylene chloride, ethylene chloride and the like; and mixtures thereof; preferably methanol, ethanol or methylene chloride; more preferably methanol.

The deprotection of compound of Formula 8 is carried out at a temperature of about 25° C. to reflux temperature; preferably at about 25° C. to 60° C.

The compound of Formula 9 obtained from step b) reaction mass may be isolated by known techniques, for example one or more solvent extractions, washings and the like.

In an embodiment, the compound of Formula 9 may be isolated by evaporating the reaction solvent under vacuum followed by extracting the product in to water immiscible organic solvent such as ethyl acetate, methylene chloride and removing the water immiscible organic solvent to obtain compound of Formula 9 as residue, which is optionally treated with a suitable hydrocarbon solvent such as hexane, heptanes, cyclohexane, methyl cyclohexane and the like and mixtures thereof to obtain compound of Formula 9 as solid compound.

Step c) of aforementioned process involves heating the compound of Formula 9 to obtain a compound of Formula 3.

The step c) of heating is carried out at a temperature of about 25° C. to about reflux temperature in a suitable solvent; preferably at about 100° C. to 150° C.

The suitable solvent used herein for step c) includes but is not limited to high boiling point solvents such as aromatic hydrocarbons such as toluene, chlorobenzene, bromo benzene, ethyl benzene, xylenes, cumene or trimethylbenzenes and the like and mixture thereof; preferably chloro benzene.

After completion of the reaction, the step c) reaction mass may be subjected to evaporation under vacuum to obtain a compound of Formula 3 as a residue, which is optionally purified using a suitable hydrocarbon solvent to obtain a solid compound of Formula 3.

Step d) of aforementioned process involves reaction of the compound of Formula 3 with a compound of Formula 4 in a suitable solvent system to obtain a compound of Formula 5.

The '517 patent discloses a process for preparation of enzalutamide, which involves cyclization of 4-isothiocyanato-2-trifluoro methyl benzonitrile of Formula 3 and N-methyl-2-fluoro-4-(1,1-dimethyl-cyanomethyl)-amino benzamide of Formula 4, which involves microwave irradiation in dimethylformamide at 100° C. for a period of about 11 hrs, which gives less yields of about only 25%. The use of special techniques such as reaction by microwave irradiation is not viable for commercial scale operations as this technique involves specialized expensive equipments. The prolonged period of microwave irradiation at 100° C. leads to formation of unwanted process impurities such as Formula 3A, Formula 3B and Formula 3C and Formula 1A in higher levels. Also the disclosed process involves tedious chromatographic purifications, which contributes significant impact on the final yield and purity, makes the process not viable for large scale manufacturing.

Generally, microwave support reactions are having many process limitations such as specific equipments, high investment costs, uncontrolled reaction temperatures and pressure and unable to trace reaction progression on multi scale reactions, thereby not suitable for commercial scale manufacturing. For example commercial microwave irradiation reactions rapidly shoot-up power outputs, which increases the reaction internal temperature and pressure, which are uncontrollable at commercial level. Further, due to vigorous heating and microwave rays most often involves formation of dark coloured residues which results nasty workup process and generally required tedious column chromatographic purification, which are not suitable for commercial scale manufacturing process.

To overcome the difficulties associated with the process described above, the inventors of the present invention have developed cyclization of 4-isothiocyanato-2-trifluoro methyl benzonitrile of Formula 3 and N-methyl-2-fluoro-4-(1,1-dimethyl-cyanomethyl)-amino benzamide of Formula 4 in a conventional synthesis method, which method involves heating and stirring in a suitable solvent and avoids microwave irradiation. The present invention overcome the aforementioned problems and yielding substantially free of one or more of process impurities and high pure final product with shorter reaction times as compared to the reported literatures.

In another embodiment, the present invention provides an improved process for the preparation of enzalutamide of Formula I, comprising:
  a2) reacting a compound of Formula 3 with a compound of Formula 4 in a suitable solvent system to obtain a compound of Formula 5, and
  b2) reacting the compound of Formula 5 with an acid to obtain enzalutamide.

The step d) or the step a2) of 4-isothiocyanato-2-trifluoro methyl benzonitrile of Formula 3 and N-methyl-2-fluoro-4-(1,1-dimethyl-cyanomethyl)-amino benzamide of Formula 4 is carried out in a suitable solvent system with heating and stirring to obtain a compound of Formula 5.

The suitable solvent of step d) or step a2) includes, but is not limited to amides, nitriles, ethers, esters, sulfones, water and mixtures thereof. The amides include, but are not limited to dimethyl formamide, dimethyl acetamide, dimethyl sulfoxide, N-methyl-2-pyrrolidone, 2-Pyrrolidone and the like; nitriles include, but are not limited to acetonitrile, propionitrile and the like; ethers include, but are not limited to tetrahydrofuran, dioxane and the like; esters include, but are not limited to methyl acetate, ethyl acetate, isopropyl acetate and the like; sulfones include, but are not limited to sulfolane, methylsulfonylmethane and the like; water and mixture thereof; preferably dimethyl formamide, dimethyl sulfoxide or tetrahydrofuran; more preferably dimethyl formamide.

The reaction of compound of Formula 3 and Formula 4 is advantageously carried out at a temperature of about 25° C. to about reflux temperature for a period of about 2 hours to about 24 hours under constant stirring; preferably at about 50° C. to 90° C. for a period of about 5 to 15 hours.

After completion of the cyclization reaction, the reaction mass as such may be used for further stage e) or step b2).

The step e) or the step b2) of reaction of compound of Formula 5 with an acid is carried out in a suitable organic solvent to obtain enzalutamide.

The suitable acid for step e) of step b2) is selected from the group consisting of hydrochloric acid, hydrobromic acid, sulfuric acid, perchloric acid, phosphoric acid, acetic acid, trifluoro acetic acid, trichloro acetic acid, methane sulfonic acid and the like and mixtures thereof; preferably hydrochloric acid.

The acid source may be in the form of an aqueous, anhydrous or gas form, for example aqueous hydrochloric acid or solvent containing hydrochloric acid or hydrochloric acid gas, preferably an aqueous hydrochloric acid can be used.

The reaction of compound of Formula 5 with an acid is carried out at a temperature of about 25° C. to about reflux temperature for a period of about 1 hour to about 12 hours; preferably at about 60° C. to 80° C. for a period of about 2 to 5 hours.

The organic solvent of step e) or step b2) includes, but is not limited to alcohols, halogenated hydrocarbons, aromatic hydrocarbons and mixtures thereof. The alcohols includes, but are not limited to methanol, ethanol, 2-methoxyethanol, n-propanol, isopropanol, butanol, n-butanol, 2-butanol, t-butanol, 1-pentanol, 2-pentanol, isopentanol and the like; halogenated hydrocarbons include, but are not limited to methylene chloride, ethylene chloride, chloroform, carbon tertrachloride and the like; aromatic hydrocarbons include, but are not limited to toluene, xylene and the like; water and mixtures thereof; preferably methanol or ethanol.

After completion of the reaction, step e) or step b2) reaction mass may be cooled to about ambient temperature and treated with a suitable water immiscible organic solvent and then optional step of washing the water immiscible organic layer with a suitable base to isolating the pure product.

The present inventors have surprisingly found that treating the step e) of step b2) reaction mass with a water immiscible organic solvent and optionally treating the product containing water immiscible organic solvent with a suitable base effectively reduces the content of one or more process impurities of Formula 1A, Formula 3A, Formula 3B and Formula 3C.

In a preferred embodiment, the product containing water immiscible organic layer, which is obtained after step e) or step b2) reaction mass, may be treated with a suitable base solution such as sodium bicarbonate, potassium bicarbonate, lithium bicarbonate, sodium carbonate, potassium carbonate, lithium carbonate, triethyl amine, ammonia and the like. At which point, the process impurities such as Formula 1A, Formula 3A, Formula 3B and Formula 3C, if any present in the water immiscible organic layer may eliminated in to base solution. Then the product containing water immiscible organic solvent may be separated off and subjected to evaporation under vacuum and then crystallization using one or more organic solvents to obtain enzalutamide.

In another embodiment, the water immiscible organic solvents used herein include, but are not limited to esters such as ethyl acetate, isopropyl acetate and the like; ethers such as methyl tertiary butyl ether, diethyl ether and the like; aromatic hydrocarbons such as toluene, xylene and the like; halogenated solvents such as methylene chloride, ethylene chloride, chloroform and the like and mixtures thereof; preferably methylene chloride or ethyl acetate.

The one or more organic solvents for crystallization includes, but are not limited to alcohols, esters, nitriles, halogenated solvents, aromatic hydrocarbons and the like and mixtures thereof. Preferably, alcohols such as methanol, ethanol, isopropanol and the like; esters such as methyl acetate, ethyl acetate, isopropyl acetate and the like; nitriles such as acetonitrile, propionitrile and the like; halogenated solvents such as methylene chloride, chloroform and the like; aromatic hydrocarbons such as toluene, xylene and the like and mixtures thereof; preferably methylene chloride, isopropanol, a mixture of isopropanol and methylene chloride or a mixture of isopropanol, methanol and methylene chloride.

The resultant enzalutamide, obtained by the aforementioned processes above, may have a chemical purity of at least about 97%, as measured by HPLC, preferably of at least about 98.5% as measured by HPLC.

In another embodiment, the present invention provides an improved process for the preparation of enzalutamide, comprising purifying the enzalutamide as obtained by the process described above or may be obtained by any known process, as a starting material or as an intermediate in one or more solvents to obtain pure enzalutamide which is having a purity equal to or greater than about 99.5% as measured by HPLC and substantially free of one or more of impurities of Formula 1A, 3A, 3B, 3C and Formula MI, MII, MIII, MIV or MV, as measured by HPLC.

In another embodiment, the present invention provides a process for purification of enzalutamide Formula I, comprising:
 a3) dissolving enzalutamide in one or more organic solvents at a' suitable temperature, and
 b3) isolating the pure enzalutamide.

The step a3) process may be involves dissolving enzalutamide in one or more organic solvents at a temperature of about ambient temperature to reflux temperature; preferably 25° C. to 90° C.

The one or more organic solvents of step a3) includes, but is not limited to alcohols, esters, nitriles, halogenated solvents, aromatic hydrocarbons and the like and mixtures thereof. The alcohols such as methanol, ethanol, isopropanol and the like; esters such as methyl acetate, ethyl acetate, isopropyl acetate and the like; nitriles such as acetonitrile, propionitrile and the like; halogenated solvents such as methylene chloride, chloroform and the like; aromatic hydrocarbons such as toluene, xylene and the like and mixtures thereof; preferably methylene chloride, isopropanol, a mixture of isopropanol and methylene chloride, or a mixture of isopropanol, methanol and methylene chloride.

The step b3) process may be involves isolation of enzalutamide substantially free from process impurities of Formula 1A, 3A, 3B, 3C and its metabolites of Formula MI, MII, MIII, MW or MV as measured by HPLC, by any conventional techniques known in the art, for example filtration. Typically, if stirring is involved, the temperature during stirring can range from about −10° C. to about 35° C.

The resultant product may optionally be further dried. Drying can be suitably carried out in a tray dryer, vacuum oven, air oven, fluidized bed drier, spin flash dryer, flash dryer and the like. The drying can be carried out at a temperature ranging from about 40° C. to about 90° C.

The present invention provides enzalutamide, obtained by the process described herein, having a chemical purity of at least about 98.5%, as measured by HPLC, preferably at least about 99.5%, as measured by HPLC; and substantially free of Formula 1A, Formula 3A, Formula 3B, Formula 3C, Formula MI, Formula MII, Formula MIII, Formula MIV or Formula MV, as measured by HPLC.

In accordance with another embodiment, the present invention provides enzalutamide containing less than 0.05%, as measured by HPLC of each of impurity of Formula 3A, 3B, 3C, 1A, MI, MII, MIII, MIV or MV.

In accordance with another embodiment, the present invention provides enzalutamide containing less than 0.2%, as measured by HPLC of total impurities of Formula 3A, 3B, 3C, 1A, MI, MII, MIII, MIV or MV.

In another embodiment, the present invention provides an improved process for the preparation of enzalutamide of Formula I, comprising:
 i) reacting 4-Amino-2-trifluoromethyl benzonitrile of Formula 2 with thiocarbonyldiimidazole (TCDI) in a suitable solvent in presence of a suitable base to obtain a compound of Formula 3,

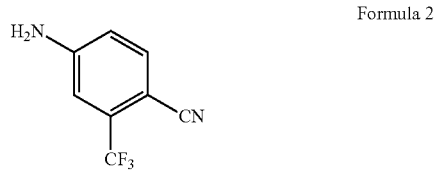

Formula 2

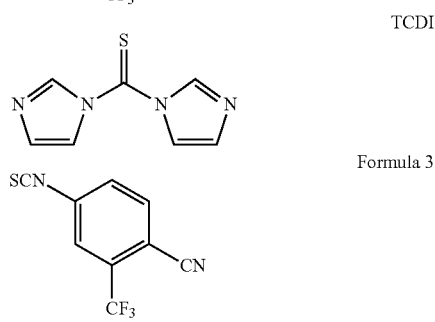

TCDI

Formula 3 ii) reacting the compound of Formula 3 with a compound of Formula 4 in a suitable solvent system to obtain a compound of Formula 5, and

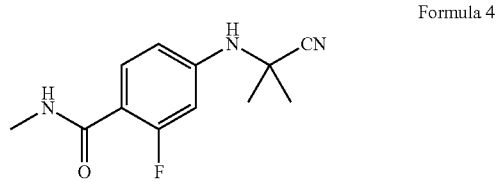

Formula 4

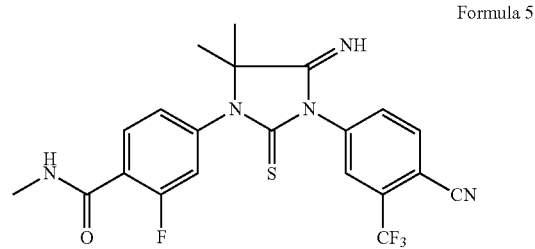

Formula 5 iii) reacting the compound of Formula 5 with an acid to obtain enzalutamide.

The reported literatures disclose a process for preparation of isothiocyanate of Formula 3 by reaction of 4-Amino-2- trifluoromethyl benzonitrile of Formula 2 with highly noxious reagent such as thiophosgene, which is an insidious poison and it generates high amount of poisonous phosgene gas and is difficult to control, particularly on commercial scale and thus requires more labor and utmost care to use.

To overcome the difficulties associated with the processes described above, the inventors of the present invention have replaced the highly noxious thiophosgene with thiocarbonyldiimidazole (TCDI), which is easy to handle and store.

Step i) of aforementioned process involves reaction of 4-Amino-2-trifluoromethyl benzonitrile of Formula 2 with thiocarbonyldiimidazole (TCDI) in a suitable solvent in presence of a suitable base to obtain a compound of Formula 3.

The suitable solvent of step i) includes, but is not limited to halogenated hydrocarbons, ethers, amides, nitriles and the like and mixtures thereof. The halogenated hydrocarbons include, but are not limited to methylene chloride, ethylene chloride, chloroform and the like and mixtures thereof; ethers include, but are not limited to dimethyl ether, diethyl ether, methyl ethyl ether, diisopropyl ether, methyl tertiary butyl ether, tetrahydrofuran, 1,4-dioxane and the like and mixtures thereof; amides include, but are not limited to dimethyl formamide, dimethyl acetamide, N-methyl pyrrolidinone and the like and mixtures thereof; nitriles include, but are not limited to acetonitrile, propionitrile and the like; water and mixtures thereof; preferably methylene chloride, tetrahydrofuran or dimethyl formamide.

The suitable base for the reaction of 4-Amino-2-trifluoromethyl benzonitrile of Formula 2 with thiocarbonyldiimidazole (TCDI) is known from any base, for instance the base is selected from the group consisting of sodium hydroxide, potassium hydroxide, lithium hydroxide, sodium carbonate, potassium carbonate, lithium carbonate, sodium bicarbonate, potassium bicarbonate, ammonia, triethylamine, N,N-diisopropyl ethyl amine and the like and mixtures thereof; preferably triethyl amine.

The step i) reaction is carried out at a temperature of about 0° C. to reflux; preferably at about 5° C. to about 35° C.

After completion of the reaction, the reaction mass may be treated with a suitable aqueous acid such as hydrochloric acid, sulfuric acid, acetic acid and the like and then separating, the organic layer. The product containing organic layer may be treated with a suitable aqueous base such as sodium bicarbonate, potassium bicarbonate, sodium carbonate, potassium carbonate and the like. Then the product containing organic solvent may be evaporated under vacuum and then crystallization using one or more organic solvents to obtain the compound of Formula 3.

The one or more organic solvents for crystallization of Formula 3 include, but are not limited to ethers, halogenated solvents, cyclic hydrocarbons and the like and mixtures thereof. Preferably, ethers such as tetrahydrofuran, methyl tertiary butyl ether, diethyl ether and the like; halogenated solvents such as methylene chloride, chloroform and the like; cyclic hydrocarbons such as hexane, cyclohexane, heptanes and the like; and mixtures thereof; preferably hexane or heptane.

Step ii) of aforementioned process involves convertion of the above obtained compound of Formula 3 in to enzalutamide by a process described as above or may be by any process known in the art.

In another embodiment, 4-isothiocyanato-2-(trifluoromethyl) benzonitrile of Formula 3 prepared by the processes described above may have a chemical purity of at least about 96-97%, as measured by HPLC and having about 3-4% impurities of Formula 3A, Formula 3B and Formula 3C as measured by HPLC.

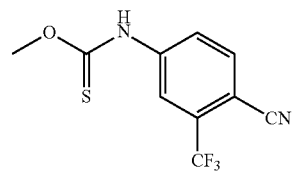

Formula 3A

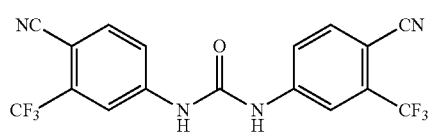

Formula 3B

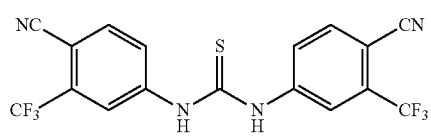

Formula 3C

The present inventors have surprisingly found that purifying the crude compound of 4-isothiocyanato-2-(trifluoromethyl) benzonitrile of Formula 3 prepared by the processes described above with a suitable solvent effectively reduces the content of impurities of Formula 3A, Formula 3B and Formula 3C.

In another embodiment, the present invention provides a process for purification of 4-isothiocyanato-2-(trifluoromethyl) benzonitrile of Formula 3, comprising:
  i) dissolving 4-isothiocyanato-2-(trifluoromethyl) benzonitrile of Formula 3 in a suitable solvent at a suitable temperature,
  ii) filtering the step i) solution,
  iii) optionally concentrating the filtrate,
  iv) cooling to less than 10° C., and
  v) isolating the pure compound of Formula 3.

The step i) process may be involves dissolving 4-isothiocyanato-2-(trifluoromethyl) benzonitrile of Formula 3 in a suitable solvent at a temperature of about ambient temperature to reflux temperature; preferably at about 50° C. to 70° C.

The suitable solvents of step i) includes, but is not limited to hydrocarbon solvents, ethers and the like and mixtures thereof. The hydrocarbon solvents include, but are not limited to hexane, cyclohexane, heptane, pentane, cyclopentane, methyl cyclohexane and the like; ethers include, but are not limited to diethyl ether, 1,4-dioxane and the like and mixtures thereof; preferably heptane, hexane or cyclohexane.

The step ii) process may be involves filtering the solution obtained in step i), at which point, the process impurity of Formula 3C, present in the compound of Formula 3 remains as un-dissolved solid and may be separated by filtration at a temperature of about ambient temperature to reflux temperature; preferably at about 50° C. to 70° C.

The compound of Formula 3 from the filtrate obtained from step ii) can be isolated by optionally concentrating the solvent from the filtrate completely under vacuum or concentrating the solvent upto minimum volume present, followed by cooling to less than 10° C. to precipitating out the product, if necessary seeding step may be involved prior to or during the cooling step iv). The resultant pure compound of Formula 3 may be isolated by known methods, for example filtration. Typically, if stirring is involved, the temperature during stirring can range from about −10° C. to about 10° C.

The present invention provides a compound of Formula 3 prepared by the process as described above having a purity of at least about 97%, as measured by HPLC, preferably at least about 98% as measured by HPLC, and more preferably at least about 99.5%, as measured by HPLC; and content of Formula 3C is less than about 0.5%, as measured by HPLC, more preferably less than about 0.2% as measured by HPLC.

In another embodiment, the present invention provides a compound of Formula 3 substantially free of one or more of following compounds:

Formula 3A

Formula 3B

Formula 3C

In another embodiment, the present invention provides enzalutamide of Formula I substantially free of one or more of following compounds:

Formula 3A

Formula 3B

Formula 3C

Formula 1A

Formula MI

Formula MII

Formula MIII

Formula MIV

Formula MV

In another embodiment, the present invention provides a compound of Formula 1A

Formula 1A

[Structure: Formula 1A]

In another embodiment, the present invention provides a compound of Formula 3A

Formula 3A

[Structure: Formula 3A]

In another embodiment, the present invention provides a compound of Formula 3B

Formula 3B

[Structure: Formula 3B]

In another embodiment, the present invention provides a compound of Formula 3C

Formula 3C

[Structure: Formula 3C]

In another embodiment, the present invention provides a compound of Formula 8

Formula 8

[Structure: Formula 8]

wherein 'P' represents hydrogen or a protective derivative thereof.

In another embodiment, the present invention provides a compound of Formula 8

Formula 8

[Structure: Formula 8]

wherein 'P' represents hydrogen, R—CO—, R—CO—O—, R—SO$_2$—; wherein R is selected from the group comprising alkyl, alkoxy, haloalkyl, aryl, aralkyl, aryloxy.

In another embodiment, the present invention provides a compound of Formula 8a

Formula 8a

[Structure: Formula 8a]

In another embodiment, the present invention provides a compound of Formula 9

Formula 9

[Structure: Formula 9]

In another embodiment, the present invention provides enzalutamide prepared according to the process described above is characterized by a powder X-ray diffraction (XRD) pattern substantially in accordance with Figure. 01.

Figure 2:
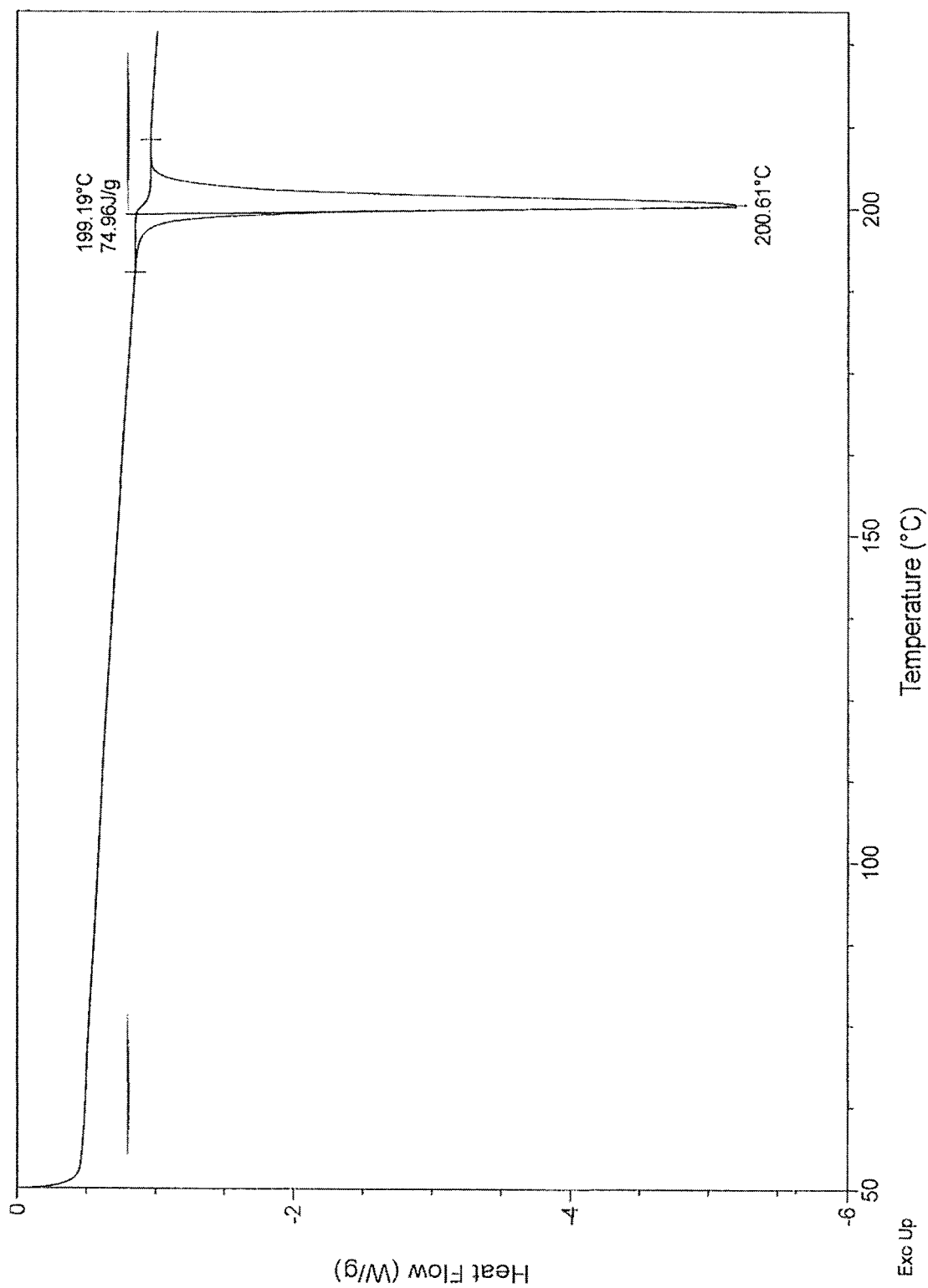
FIG. 2 is the characteristic differential scanning calorimetric (DSC) thermogram of enzalutamide, prepared according to Example 6.

In another embodiment, the present invention provides enzalutamide prepared according to the process described above is characterized by a differential scanning calorimetry (DSC) substantially in accordance with Figure. 02.

In another embodiment, the present invention provides crystalline enzalutamide characterized by a powder X-ray diffraction (XRD) pattern having the peaks are tabulated below:

| 2θ | d-value | I/Io |
| --- | --- | --- |
| 9.8 | 9.01 | 13 |
| 12.3 | 7.1 | 15 |
| 13.1 | 6.7 | 100 |
| 13.48 | 6.5 | 23 |
| 14.34 | 6.1 | 18 |
| 14.96 | 5.9 | 13 |
| 16.68 | 5.3 | 40 |
| 17.38 | 5.0 | 13 |
| 18.82 | 4.7 | 44 |
| 19.50 | 4.5 | 20 |
| 21.16 | 4.1 | 46 |
| 21.76 | 4.0 | 33 |
| 22.78 | 3.9 | 43 |
| 23.10 | 3.8 | 18 |
| 24.36 | 3.6 | 28 |
| 24.84 | 3.5 | 18 |
| 25.44 | 3.4 | 21 |
| 26.40 | 3.3 | 33 |
| 27.92 | 3.1 | 14 |
| 28.84 | 3.0 | 15 |

-continued

| 2θ | d-value | I/Io |
|---|---|---|
| 29.70 | 3.0 | 14 |
| 31.18 | 2.8 | 16 |
| 32.44 | 2.7 | 16 |
| 33.14 | 2.7 | 16 |

In another embodiment, the present invention provides enzalutamide and its intermediates, obtained by the above process, as analyzed using high performance liquid chromatography ("HPLC") with the conditions are tabulated below:

| | |
|---|---|
| Column | Inertsil ODS-3V, (250 × 4.6 ) mm, 5 μm |
| Column temperature | 40° C. |
| Mobile phase | Mobile phase-A: buffer: acetonitrile |
| | Mobile phase-B: buffer: acetonitrile: methanol |
| Buffer | Sodium perchlorate in water (pH to 2.5 with perchloric acid) |
| Diluent | Mixture of water and acetonitrile 50:50 (v/v). |
| Flow rate | 0.7 mL/min |
| Wavelength | 235 nm |
| Injection Volume | 10 μL |
| Elution | Gradient |

As used herein the word "substantially free" refers to enzalutamide having less than 0.1% of one or more of process impurities by HPLC, preferably less than 0.05% by HPLC.

Another embodiment of the present invention is directed to a pharmaceutical composition containing at least the substantially pure enzalutamide and at least one pharmaceutically acceptable excipient. Such pharmaceutical composition may be administered to a mammalian patient in any dosage form, e.g., capsule, liquid, powder, elixir, injectable solution, etc.

EXAMPLES

The present invention will now be further explained in the following examples describing in detail the preparation of the said salt forms. However, the present invention should not be construed as limited thereby. One of ordinary skill in the art will understand how to vary the exemplified preparations to obtain the desired results.

Example 1: Preparation of Isothiocyanate of Formula 3

To a 250 ml round bottom flask fitted with a mechanical stirrer, thermometer socket was charged methylene chloride (200 ml), 4-Amino-2-trifluoromethyl benzonitrile of Formula 2 (100 gms) and 1,1-Thiocarbonyldiimidazole (105.3 gms) at room temperature. The reaction mass temperature was cooled to 10° C. to 15° C., was added triethylamine (108.7 gms) slowly at 10° C. to 15° C. After addition of the triethylamine reaction mass becomes homogeneous solution. The reaction mass was stirred for 2 to 2.5 hours at 25° C. to 30° C. After completion of the reaction charged methylene chloride (300 ml) and cooled to −10° C. to about 0° C., was charged precooled aqueous hydrochloric acid (dissolved 260 ml conc. HCl and 740 ml water) and stirred for 15-20 min. Separated the organic and aqueous layers. The organic layer washed with 7% aq. sodium bicarbonate solution (dissolved 35 gms sodium bicarbonate in 500 ml water and stir well) followed by brine solution (1×500 ml). The organic layer was distilled under vacuum and was recrystallized from n-heptane to obtain the title compound as a solid and dried under vacuum at a temperature about 25-30° C. Yield: 110.0 gms; Purity by HPLC: 95.0%; Formula 3A by HPLC: 0.02%; Formula 3B by HPLC: Not detected; Formula 3C by HPLC: 3%.

Example 2: Preparation of N-{[4-cyano-3-(trifluoromethyl) phenyl] carbamothioyl} benzamide of Formula 8a To a 3 lit round bottom flask fitted with a mechanical stirrer, thermometer, reflux condenser was charged acetone (400 ml), ammonium thiocyanate (57 gms) at 25° C. to 30° C. and stirred for 10-15 min at same temperature. To the reaction mass benzoyl chloride (98.1 gms) was added over a period of 30-45 min at 25° C. to 30° C. Reaction mass was heated to 55° C. to 60° C. and stirred for 10-15 min at same temperature. To the reaction mass 4-Amino-2-trifluoromethyl benzonitrile (100 gms was dissolved in 400 ml acetone) was added over a period of 1 hr at 55° C. to 60° C. and stirred for 3-4 hr. After completion of the reaction, the reaction mass was cooled to 25° C.-30° C. and charged chilled water (1 lit), stirred for 1 hr at 25° C.-30° C. The precipitated solid was filtered and washed with water (200 ml). Yield: 140 gms (wet).

Example 3: Preparation of 1-[4-cyano-3-(trifluoromethyl)phenyl]thiourea of Formula 9

To a 2 lit round bottom flask fitted with a mechanical stirrer, thermometer, reflux condenser was charged methanol (400 ml), above ex-2 wet compound at 25° C. to 30° C. and stirred for 10-15 min at same temperature. To the reaction mass 3M sodium hydroxide (350 ml) was added over a period of 1 hr at 25° C. to 30° C. Reaction mass was heated to 55° C. to 60° C. and stirred for 3-4 hr at same temperature. After completion of the reaction, reaction mass was subjected to concentration under vacuum at 40° C.-45° C. to obtain residue. To the residue water (400 ml) and ethyl acetate (800 ml) was charged at 25° C.-30° C. and stirred for 30 min at same temperature and organic layer was separated off, washed with water (200 ml) and brine (200 ml) and distilled out solvent completely under vacuum at below 50° C. To the reaction mass cyclohexane (900 ml) was charged and stirred for 30 min at 25° C.-30° C. and precipitated solid was filtered and washed with cyclohexane (100 ml). The wet product was dried at 40° C. to 45° C. under vacuum to provide the title compound as solid. Yield: 125 gms; Purity by HPLC: 98%.

Example 4: Preparation of 4-isothiocyanato-2-(trifluoromethyl) benzonitrile of Formula To a 2 lit round bottom flask fitted with a mechanical stirrer, thermometer, reflux condenser was charged chlorobenzene (1.5 lit), 1-[4-cyano-3-(trifluoromethyl) phenyl] thiourea of Formula 9 (100 gms) at 25° C.-30° C. and stirred for 10-15 min at same temperature. Reaction mass was heated to 130° C. to 135° C. and stirred for 18-20 hr at same temperature. After completion of the reaction, reaction mass was subjected to concentration under vacuum at 40° C.-45° C. and charged heptane (200 ml) and distilled out solvent completely under vacuum at 40° C.-45° C. to obtain residue. Purity by HPLC: 96.0%; Formula 3C by HPLC: 4.0%.

Purification of Formula 3

To a 2 lit round bottom flask fitted with a mechanical stirrer, thermometer, reflux condenser was charged heptane (1200 ml) and was heated to 65° C.-70° C. and stirred for 1 hr at same temperature. Filtered off the un-dissolved material at 65° C.-70° C., obtained filterate was subjected to concentration under vacuum at 40° C.-45° C. until ~250 ml of solvent remains in the flask. Cooled the reaction mass to 0° C.-5° C. and seed compound (10 mg) was added and stirred for 30-45 min at same temperature. The precipitated solid was filtered and washed with chilled heptane (100 ml). The wet product was dried at about 30° C. to about 35° C. under vacuum to provide the title compound. Yield: 60.0 gms; Purity by HPLC: 99.5%; Formula 3C by HPLC: 0.5%.

Example 5: Preparation of Enzalutamide

To a 100 ml round bottom flask fitted with a mechanical stirrer, reflux condenser, thermometer socket was charged dimethyl formamide (30 ml), 4-isothiocyanato-2-trifluoro methyl benzonitrile of Formula 3 (15 gms) and N-methyl-2-fluoro-4-(1,1-dimethyl-cyanomethyl)-amino benzamide of Formula 4 (29.1 gms) at room temperature. The reaction mass temperature was raised to 80° C. to 85° C. and stirred for 7 hrs. After completion of the reaction mass, temperature was sequentially cooled to room temperature and followed by charged methanol (75 ml), 1N aqueous hydrochloric acid (75 ml) and reaction mass temperature was raised to 70° C. to 75° C. and stirred for 2 hrs. After completion of the reaction the temperature of the reaction mass was cooled to 20° C. to 25° C. and the reaction mass was extracted with dichloromethane (2×150 ml). To the combined organic layer given saturated sodium bicarbonate solution washings (2×150 ml) and water washing (1×150 ml). Distilled the organic layer under vacuum to obtain a residue and to the obtained residue was added isopropyl alcohol (290 ml) and heated to 70° C. to 75° C. to obtain a clear solution, then the reaction mass temperature was allowed to cool to 0-5° C. and precipitated solid was filtered to obtain title compound and dried under vacuum at a temperature about 50-55° C. Yield: 10.0 gms; Purity by HPLC: 97.0%; Formula 1A by HPLC: 1%; Formula 3A by HPLC: 0.8%; Formula 3B by HPLC: 0.5%; Formula 3C by HPLC: 0.7%.

Example 6: Purification of Enzalutamide

To a 250 ml round bottom flask fitted with a mechanical stirrer, reflux condenser, thermometer socket was charged methylene chloride (120 ml) and enzalutamide obtained from example-2 (10 gms) was heated to about 35° C. to about 40° C. and maintained for 20 min. To the clear solution was charged activated carbon and filtered, followed by normal distillation of methylene chloride to obtain a residue. To the residue was charged methanol (10 ml) and isopropyl alcohol (100 ml) and heated to about 70° C. to about 75° C. to obtain a clear solution. Then the clear solution was allowed to cool to about 25-30° C. and precipitated solid was filtered.

The above obtained wet compound was dissolved in methylene chloride (120 ml) heated to about 35° C. to about 40° C. and maintained for 20 min. To the clear solution was charged activated carbon and filtered, followed by normal distillation of methylene chloride to obtain a residue. To the residue was charged isopropyl alcohol (120 ml) and heated to about 80-83° C. to obtain clear solution, distilled isopropyl alcohol (10 ml) under normal atmospheric pressure (reaction volume-100 ml) and reaction mass was allowed to cool to about 25-30° C., precipitated solid was filtered and dried under vacuum at a temperature about 50-55° C. to obtain title compound as a solid. Yield: 9.0 gms; Purity by HPLC: 99.5%; Formula 1A by HPLC: 0.10%; Formula 3A by HPLC: 0.10%; Formula 3B by HPLC: 0.15%; Formula 3C by HPLC: Not detected; Formula MI by HPLC: Not detected; Formula MII by HPLC: Not detected; Formula MIV by HPLC: 0.05%; XRPD is set forth in FIG. 1; DSC is set forth in FIG. 2.

Example 7: Preparation of Enzalutamide

To a 2 lit round bottom flask fitted with a mechanical stirrer, reflux condenser, thermometer socket was charged dimethyl formamide (200 ml), 4-isothiocyanato-2-trifluoro methyl benzonitrile of Formula 3 (100 gms) and N-methyl-2-fluoro-4-(1,1-dimethyl-cyanomethyl)-amino benzamide of Formula 4 (155.2 gms) at room temperature. The reaction mass temperature was raised to 60° C. to 65° C. and stirred for 12 hrs. After completion of the reaction mass, temperature was sequentially cooled to room temperature and followed by charged methanol (500 ml), 1N aqueous hydrochloric acid (500 ml) and reaction mass temperature was raised to 70° C. to 75° C. and stirred for 2-3 hrs. After completion of the reaction the temperature of the reaction mass was cooled to 25° C. to 30° C. and was charged methylene chloride (1000 ml) at same temperature. Reaction mass was washed with 7% sodium bicarbonate solution (2×1 lit), water (500 ml) and brine solution (500 ml) sequentially. Then the resultant organic layer was treated with carbon and distilled methylene chloride under vacuum at below 45° C. and degassed residue at 60-65° C. To the obtained residue was added isopropanol (2×300 ml) at 60-65° C. and distilled the solvent completely under vacuum at 60-65° C. to obtain residue. To residue was added isopropanol (flit) and cooled to 25-30° C., charged methylene chloride (100 ml). Reaction mass was heated to 60-65° C. and stirred for 30 min at same temperature. Cooled reaction mass to 0-5° C. and stirred for 2 hrs to precipitate solids. Filtered the obtained solids and washed with isopropanol (2×200 ml).

To the above wet compound was added methylene chloride (1 lit) and given carbon treatment at 35-40° C. and distilled methylene chloride under vacuum at below 45° C. to obtain residue. To the residue was added isopropanol (1 lit), methanol (100 ml) and methylene chloride (25 ml) and heated to 70-75° C. and stirred for 30 min at same temperature. Reaction mass was cooled 25-30° C. and stirred for 90 min at same temperature. Filtered, the obtained solids and washed with isopropanol (100 ml), dryed at 90-95° C. to obtain title compound. Yield: 90 gms, Purity by HPLC: 99%.

Example 8: Purification of Enzalutamide

To a 2 lit round bottom flask fitted with a mechanical stirrer, reflux condenser, thermometer socket was charged methylene chloride (800 ml) enzalutamide (100 gms) and given carbon treatment at 30-35° C. Reaction mass was distilled completely at below 45° C. further co-distilled with isopropanol (200 ml) at 85° C. To the reaction mass was added isopropanol (1.6 lit) and stirred for 15 min at 80-85° C. Reaction mass was cooled to 25-30° C. and stirred for 2 hrs at same temperature. Filtered the obtained solids and washed with isopropanol (200 ml), dryed at 90-95° C. to obtain title compound. Yield: 95 gms; Purity by HPLC: 99.8%; Formula 1A by HPLC: Not detected; Formula 3A by HPLC: Not detected; Formula 3B by HPLC: Not detected;

Formula 3C by HPLC: Not detected; Formula MI by HPLC: Not detected; Formula MII by HPLC: 0.07%; Formula MIV by HPLC: 0.05%.

Example 9: Characterization of Impurities of Formula IA, Formula 3A, Formula 3B and Formula 3C by $^1$H-NMR Formula 1A

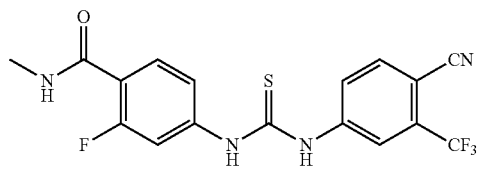

$^1$HNMR (DMSO-d6): 8.31 (d, 1H, J = 1.8 Hz), 8.11 (d, 1H, J = 8.4 Hz), 8.2 (dd, 1H, J = 8.4, 1.8 Hz), 7.34 (dd, 1H, J = 8.1, 1.8 Hz), 7.66 (m, 1H), 7.62 (m, 1H), 2.78 (d, 3H, J = 4.5), 10.66 (br, 2H), 8.16 (m, 1H); MS (ESI)[M + H$^+$]$^+$: 397

Formula 3A

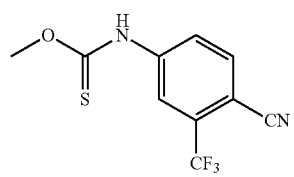

$^1$HNMR (CDCl$_3$): 8.5 (S, 1H), 7.90 to 7.79 (3H), 4.17 (S, 3H), 1.60 (S, 2H); MS (ESI)[M + H$^+$]$^+$: 261

Formula 3B

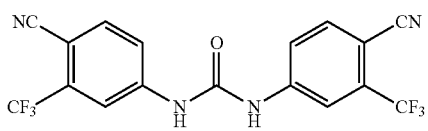

$^1$HNMR (Acetone-d6): 8.11 (d, 2H, J = 1.8), 7.77 (d, 2H, J = 8.7), 7.85 (dd, 2H, J = 8.4, 1.2); MS (ESI)[M + H$^+$]$^+$: 397

Formula 3C

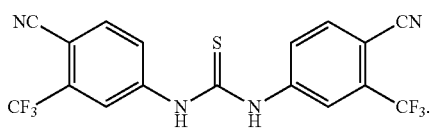

$^1$HNMR (DMSO-d6): 10.95 (S, 2H), 8.28 (d, 2H), 8.2 (d, 2H), 8.0 (dd, 2H)

It will be understood that various modifications may be made to the embodiments disclosed herein. Therefore the above description should not be constructed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A process for the preparation of enzalutamide of Formula I,

Formula I

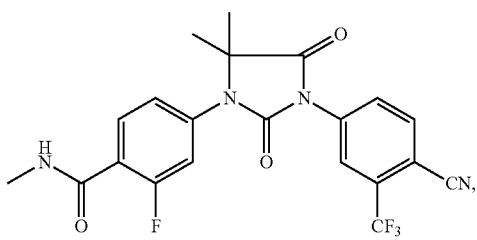

comprising:

a) reacting 4-amino-2-trifluoromethyl benzonitrile of Formula 2 with a source of isothiocyanate of Formula P-NCS, to obtain a compound of Formula 8, wherein 'P' represents hydrogen or a protective group, Formula 2

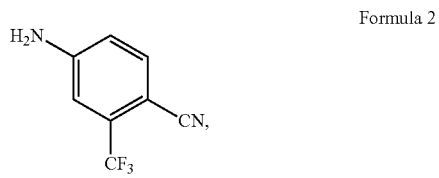

Formula 8

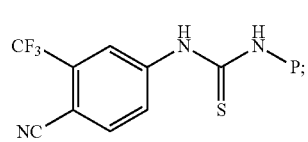

b) optionally deprotecting the compound of Formula 8 to obtain a compound of Formula 9, Formula 9

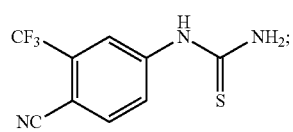

c) heating the compound of Formula 9 to obtain a compound of Formula 3,

Formula 3

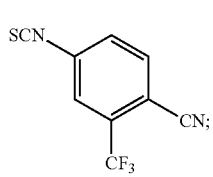

d) reacting the compound of Formula 3 with a compound of Formula 4 in a solvent system to obtain a compound of Formula 5,

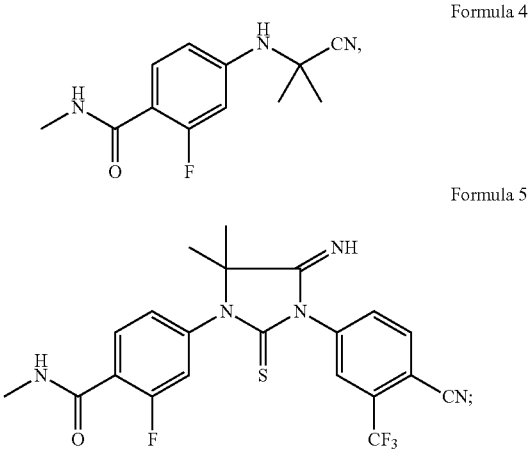

and e) reacting the compound of Formula 5 with an acid in an organic solvent to obtain enzalutamide.

2. The process of claim 1, wherein the protective group is selected from one of R—CO—, R—CO—O—, and R—SO₂—, and wherein 'R' is selected from one of an alkyl, an alkoxy, a haloalkyl, an aryl, an aralkyl and an aryloxy.

3. The process of claim 1, wherein 'P' is the protective group benzoyl.

4. The process of claim 1, wherein the source of isothiocyanate is benzoyl isothiocyanate.

5. The process of claim 1, wherein the step a) is carried out in the presence of a solvent.

6. The process of claim 5, wherein the solvent of the step a) is selected from one of acetone, methyl tertiary butyl ether, and tetrahydrofuran.

7. The process of claim 1, wherein the deprotection is carried out in the presence of a base.

8. The process of claim 7, wherein the base is selected from one of sodium hydroxide and potassium hydroxide.

9. The process of claim 1, wherein the step c) is carried out in a solvent selected from one of toluene, chlorobenzene, bromo benzene, ethyl benzene, xylenes, cumene, trimethylbenzene and mixtures thereof.

10. The process of claim 1, wherein the step c) of heating is carried out at a temperature of about 100° C. to 150° C.

11. The process of claim 1, wherein the step c) is carried out at a temperature of about 130-135° C. in chlorobenzene.

12. The process of claim 1, wherein the solvent of step d) is selected from one of an amide, a nitrile, an ether, an ester, a sulfone, and mixtures thereof.

13. The process of claim 1, wherein the solvent of the step d) is selected from one of dimethyl formamide, dimethyl sulfoxide, tetrahydrofuran, and mixtures thereof.

14. The process of claim 1, wherein the step d) is carried out under stirring at a temperature of about 50° C. to 90° C.

15. The process of claim 1, wherein the acid is selected from one of hydrochloric acid, hydrobromic acid, sulfuric acid, perchloric acid, phosphoric acid, acetic acid, trifluoro acetic acid, trichloro acetic acid, methane sulfonic acid, and mixtures thereof.

16. The process of claim 1, wherein the organic solvent is selected from one of an alcohol, a halogenated hydrocarbon, an aromatic hydrocarbon, and mixtures thereof.

17. The process of claim 1, wherein the acid is hydrochloric acid and the organic solvent is methanol.

18. The process according to claim 1, further comprising:
f) combining the enzalutamide with at least one pharmaceutically acceptable excipient.

* * * * *